United States Patent [19]

Kligman

[11] Patent Number: 4,888,342
[45] Date of Patent: * Dec. 19, 1989

[54] METHODS FOR TREATMENT OF SUNDAMAGED HUMAN SKIN WITH RETINOIDS

[76] Inventor: Albert M. Kligman, c/o University of Pennsylvania, Room 244, Medical Education Bldg./GM, 36th & Hamilton Walk, Philadelphia, Pa. 19104

[*] Notice: The portion of the term of this patent subsequent to Jul. 29, 2003 has been disclaimed.

[21] Appl. No.: 228,212
[22] PCT Filed: Jul. 15, 1987
[86] PCT No.: PCT/US87/01698
§ 371 Date: Mar. 8, 1988
§ 102(e) Date: Mar. 8, 1988
[87] PCT Pub. No.: WO88/00466
PCT Pub. Date: Jan. 28, 1988

Related U.S. Application Data

[63] Continuation-in-part of Ser. No. 886,595, Jul. 16, 1986, abandoned, which is a continuation-in-part of Ser. No. 759,505, Jul. 26, 1985, Pat. No. 4,603,146, which is a continuation-in-part of Ser. No. 610,711, May 16, 1984, abandoned, which is a continuation-in-part of Ser. No. 297,388, Aug. 28, 1981, abandoned.

[51] Int. Cl.⁴ ..................... A61K 31/07; A61K 31/40
[52] U.S. Cl. ................................. 514/419; 514/443; 514/469; 514/489; 514/569; 514/621; 514/685; 514/725
[58] Field of Search ............... 514/419, 443, 469, 489, 514/569, 621, 685, 725

[56] References Cited

U.S. PATENT DOCUMENTS

| | | | |
|---|---|---|---|
| 3,856,934 | 12/1974 | Kligman | 424/62 |
| 3,906,108 | 9/1975 | Felty | 424/318 |
| 4,603,146 | 7/1986 | Kligman | 514/559 |

FOREIGN PATENT DOCUMENTS

| | | |
|---|---|---|
| 887713 | 11/1979 | Belgium . |
| 2240187 | 2/1974 | Fed. Rep. of Germany . |
| 1297730 | 5/1962 | France . |
| 2405068 | 4/1979 | France . |
| 906000 | 9/1962 | United Kingdom . |
| 1239965 | 7/1971 | United Kingdom . |
| 1466062 | 3/1977 | United Kingdom . |

OTHER PUBLICATIONS

Kligman, A. M. et al., "A New Formula for Depigmenting Human Skin", *Archives of Dermatology*, 111:40-48 (1975).
Kligman, A. M. et al., "Topically Applied Tretinoin for Senile (Solar) Comedones", *Archives of Dermatology*, 104:420-421 (1971).
Robinson, T. A. et al., "Treatment of Solar Keratoses of the Extremities with Retinoic Acid and 5-Fluorouracil," *British Journal of Dermatology*, 92:703-705 (1975).
Kligman, L. H. et al., "The Effect on Rhino Mouse Skin of Agents which Influence Keratinization and Exfoliation," *Journal of Investigative Dermatology*, 73:354-358 (1979).
Saline, C., "Adventures in the Skin Trade," *Philadelphia Magazine*, pp. 120-133 (1980).
"Industry Happenings," *Drug & Cosmetics Industries*, page 86, (1985).
Pawson, B. A., et al., "Retinoids at the Threshold: Their Biological Significance and Therapeutic Potential," *Journal of Medicinal Chemistry*, 25:1269-1277 (1982).
Symposium Publication-J. H. Saurat, Editor, "Retinoids: New Trends in Research and Therapy," Karger Publishing Company (1985).
Thomas, J. R. et al., "The Therapeutic Uses of Topical Vitamin A Acid," *Journal of American Academy of Dermatology*, 4:505-513 (1981).
Mayer, H., et al., "Retinoids, a New Class of Compounds with Prophylactic and Therapeutic Activities in Oncology and Dermatology," *Experientia*, Vol. 34 (1978).
Trown, P. W., "Relationship Between Binding Affinities to Cellular Retinoic Acid-Binding Protein and In Vivo and In Vitro Properties for 18 Retinoids," *Cancer Research*, vol. 40, p. 212 (1980).

*Primary Examiner*—Leonard Schenkman
*Attorney, Agent, or Firm*—Panitch, Schwarze Jacobs and Nadel

[57] ABSTRACT

Various effects of photoaging or sundamage of skin including impairment of differentiation of epidermal epithelial cells and loss of collagen fibers, abnormal changes in elastic fibers and deterioration of small blood vessels in the dermis of the skin are retarded by applying topically to the epidermis in a maintenance therapy program effective amounts of retinoids including retinoid derivatives and stereoisomers thereof such that epithelial growths are substantially reduced and prevented and the skin substantially regains and maintains its firmness, turgor and elasticity. Moreover, with persistent treatment dermal blood cells and vessels increase and the epidermis and dermis thicken, resulting in improved ability of the skin to sense, resist and recover from irritation or injury. Further, hyperpigmentation, lines and wrinkles due to aging are reduced and prevented. The treatment is particularly useful for human facial skin and preferably applied in amounts insufficient to cause excessive irritation.

4 Claims, No Drawings

METHODS FOR TREATMENT OF SUNDAMAGED HUMAN SKIN WITH RETINOIDS

CROSS-REFERENCE TO RELATED APPLICATIONS

This application is a continuation-in-part of my co-pending application Ser. No. 886,595, filed July 16, 1986 now abandoned for "Methods for Treatment of Sundamaged Human Skin with Retinoids," now abandoned, which was in turn a continuation-in-part of application Ser. No. 759,505, filed July 26, 1985, now U.S. Pat. No. 4,603,146, which was a continuation of application Ser. No. 610,711, filed May 16, 1984, now abandoned, which in turn was a continuation-in-part of application Ser. No. 297,388, filed Aug. 28, 1981, now abandoned. This application is also related to my co-pending U.S. application Ser. No. 205,057, filed June 3, 1988.

FIELD OF THE INVENTION

This invention relates to methods using retinoids to retard the effects of aging of the skin and generally improve the quality of the skin, particularly human facial skin.

BACKGROUND OF THE INVENTION

Caucasians who have had a good deal of sun exposure in childhood will show the following gross cutaneous alterations in adult life: wrinkling, leatheriness, yellowing, looseness, roughness, dryness, mottling (hyperpigmentation) and various premalignant growths (often subclinical). These changes are most prominent in light-skinned persons who burn easily and tan poorly. The baleful effects of sunlight are cumulative, increasing with time often referred to as "photoaging". Although the anatomic degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness, loss of elasticity are very late changes.

Retinoids (e.g. Vitamin A and its derivatives) are substances which are known to have a broad spectrum of biological activity. More specifically, these substances affect cell growth, differentiation and proliferation. Retinoids affect the differentiation, maintenance, and proliferation of many types of cells whether they are of ectodermal, endodermal or mesodermal origin; whether they are epithelial, fibroblastic or mesenchymal; or whether they are neoplastic, preneoplastic or non-neoplastic. At present, retinoids have found clinical utility in the treatment of severe cystic acne, psoriasis, and other disorders of keratinization. Possible uses of retinoids are being explored in the prophylaxis and treatment of cancer. For a review of developments in retinoid therapy, see Pawson, B. A. et al, "Retinoids at the Threshold: Their Biological Significance and Therapeutic Potential", *Journal of Medicinal Chemistry* 25:1269-1277 (1982).

The present status of retinoids in research and clinical medicine can be found in the publication of a symposium held in Geneva: J. H. Saurat, Editor, "Retinoids: New Trends in Research and Therapy," Karger Publishing Co. (1985).

It is known to use certain retinoids, particularly vitamin A acid, topically for treatment of acne as set forth in my U.S. Pat. No. 3,729,568. Other known topical uses of vitamin A acid were reviewed by Thomas, J. R., et al, "The Therapeutic uses of Topical Vitamin A Acid", *Journal of American Academy of Dermatology* 4:505-516 (1981) include, in addition to acne treatment, treatment of senile comedones, nevus comedonicus, linear verrucous nevus, plantar warts, pseudofolliculitis, keratoacanthoma, solar keratosis of extremities, callosites, keratosis palmaris et plantaris, Darier's disease, ichthyosis, psoriasis, acanthosis nigricans, lichen planus, molluscum contagiosum, reactive perforating collagenosis, melasma, corneal epithelial abrasion, geographic tongue, Fox-Fordyce disease, cutaneous metastatic melanoma and keloids or hypertrophic scars.

It is believed that retinoids influence ultrastructural and proliferative properties of epidermal cells. However, these prior art uses of vitamin A acid have generally involved short term treatments in which relatively high concentrations of retinoic acid are applied (i.e. sufficient to cause significant irritation and often peeling) in order to obtain a quick therapeutic effect of the particular condition, such as removal of comedones, as opposed to long-term treatment of normal aging or photoaging skin.

My U.S. Pat. No. 4,603,146 discloses methods for treating sundamaged human skin topically with vitamin A acid in an emollient vehicle in such amounts as to be essentially nonirritating to the skin. This treatment causes the skin, particularly human facial skin, to substantially regain and maintain its firmness, turgor and elasticity by retarding and reversing the skin's loss of collagen fibers, abnormal changes in elastic fibers, deterioration of small blood vessels, epidermal atrophy and formation of abnormal epithelial growths.

BRIEF SUMMARY OF THE INVENTION

The present invention relates to the use of other retinoids, as hereinafter defined, in moderating and preventing the aging changes of the exposed (sundamaged) areas of the skin, especially the face. In particular, the methods of the present invention retard the effects of photoaging of the skin due to thinning and abnormal differentiation of the epidermis, inter alia. In general, the present invention relates to methods for retarding and reversing the loss of collagen fibers, abnormal changes in elastic fibers, deterioration of small blood vessels, and formation of abnormal epithelial growths in sundamaged human skin, comprising applying topically to the surface of the skin a composition comprising effective amounts of a retinoid in an emollient vehicle in a program of maintenance therapy, whereby the skin substantially regains and maintains its firmness, turgor and elasticity during the therapy, the composition and amounts of retinoid therein being selected so as to provide a sub-irritating dose for application.

More specifically, the methods comprise the topical application to the surface of the skin of effective amounts of retinoids in a program of maintenance therapy, whereby epithelial neoplasms (basal and squamous cell cancers) and preneuplastic growths (actinic keratoses) are substantially prevented. Also, the skin significantly regains and maintains its firmness, turgor and elasticity during the therapy. Effacement of fine wrinkles is an important clinical effect. Generally, the maintenance therapy is begun in adult life when epithelial growths and other aging changes begin to appear clinically. Pigmentary blotching and mottling are also alleviated.

The retinoids may be applied to the skin in any non-toxic, dermatologically acceptable vehicle, preferably a non-volatile, emollient or lubricating vehicle, in an amount and at a frequency which are insufficient to cause irritation of the skin. Generally, the concentrations are low but may be suitably varied depending on the relative strength of the applied retinoid.

DETAILED DESCRIPTION OF THE PREFERRED EMBODIMENTS

The purpose of this invention is to moderate and retard the aging changes in the skin by topical application of retinoids beginning in young adult life when aging changes (sundamage) first become evident clinically. Certain anatomic alterations can be corrected and at least partially reversed, accompanied by improvement in the appearance of the skin.

The invention accomplishes two goals. First, a prophylactic effect in preventing progression and worsening of the damage with the passage of time. Secondly, various abnormalities are corrected and modified to the extent that the structure and function of the skin acquires the characteristics of younger (undamaged) skin.

AGE ASSOCIATED STRUCTURAL CHANGES

Although many of the effects of the aging of the human skin are the result of underlying structural changes which build up over a period of years and can only be detected histologically prior to young adult life, these changes and effects begin to appear clinically in young adults, namely those between about 20 and 30 years of age, and are generally evident about middle age, namely between about 35 and 45 years of age, and become more and more evident and pronounced thereafter, especially in persons excessively exposed to sunlight. The more apparent effects of aging have already been referred to above; and each is associated with one or more underlying structural changes in the skin. For example, blotchiness or mottling(hyperpigmentation) is due to accumulation of melanin in the basal cells of the epidermis. This happens because the reproduction of the cells slows down greatly with aging, allowing them much longer time to receive melanin from the surrounding pigment-producing melanocytes. By stimulating the proliferation of basal cells, pigment retention is prevented.

In addition to obvious cosmetic improvements in the skin, there are a number of other changes which are more important though less apparent, including loss of sensory acuity, reduced wound healing, decreased blood flow and decrease in the thickness of the skin. Older people have less sensitivity to pain and a longer response time. Thus, pain due to irritation or injury is not felt as soon or to the same extent as in young people with the result that superficially minor but potentially serious injuries may be sustained without the individual being aware of the injury until serious damage has occured.

The surface temperature of the skin in older people is lower than the skin temperature in younger people, so that they often feel cold. This is one reason why the elderly retire to the sunbelt. Anatomically there is a great loss of small blood vessels so that physiologically the blood flow through the skin is greatly reduced. The skin becomes paler and cooler. Furthermore, the decreased blood supply decreases the rate at which irritants and toxins are cleared from the skin. Dangerous build-up of toxic agents can result.

Still further, the skin of older people is more easily torn than that of younger people, since both the epidermis and dermis become thinner with age and the fibrous matrix becomes structurally inferior. As a result, there is less bulk to protect underlying organs and therefore more risk of serious injury. Moreover, when wounds or injuries are sustained, healing of the wounds is much slower in older people.

The underlying causes of the above gross skin effects may be understood more readily from the following discussion of the specific changes in the epidermis and dermis as aging progresses.

1. Epidermis

With increasing age and exposure of a human to sun and other environmental traumas, cells divide at a slower rate (decreased capacity to renew themselves). They show marked irregularities in size, shape and staining properties; orderliness (polarity) from below to above is lost. The thickness of the epidermis decreases (atrophy). The horny layer which comprises the barrier against water loss and penetration of chemicals becomes abnormal due to the shedding (exfoliation) of cells in large groups or clusters instead of as individual cells, resulting in roughness, scaling and dryness. There is loss of the orderly transformation of living epithelial cells into cornified dead cells which are shed at the surface, that is, differentiation is impaired. Aberrant differentiation results in numerous foci of abnormal epithelial growths or tumors, the most frequent of which are actinic keratoses. After many years these can transform into frank skin cancers called basal cell and squamous cell cancers. Pigment producing cells (melanocytes) can also become altered, forming flat, dark growths (lentigo melanoma) which may progress to malignant melanoma. The cells which make up these premalignant growths are eliminated by topical application of retinoids.

2. Dermis

The cells which make up the fibers of the dermis become smaller and sparser with increasing age, usually in sundamaged facial skin. There is a great loss of collagen fibers resulting in looseness and easy stretchability of the skin; elastic fibers become abnormal so that the skin does not promptly snap back after being stretched. Since the fibrous components comprise more than 90% of the bulk of skin of which 95% is collagen, the degradation of these fibers, especially collagen, is mainly responsible for wrinkling, laxness and loss of elasticity.

Small blood vessels become thin walled, dilated and often ruptured. Vascular supply thereby becomes compromised.

Beneficial Effects of Retinoids in Accordance With the Present Invention (a) Increased proliferative activity of epidermal cells. This results in thickening of the epidermis with correction of atrophy. Cell renewal is quickened so that cells divide at a rate typical of younger skin. Treatment with retinoids in accordance with the invention can double the thickness of the epidermis. The stimulation of cell growth also results in faster wound healing. Experiments have been performed wherein blisters have been raised and the roofs cut off of the skins of individuals of various ages. Healing takes place in 2 or 3 weeks in young people, but takes much longer in older persons. Application of the retinoid tretinoin, vitamin A acid or all-trans retinoic acid before raising the blister halves the healing time.

(b) Correction of abnormalities of differentiation. Retinoids regulate and control the physiologic behavior of epithelial tissue, assuring its stability and integrity. They correct and normalize abnormalities of differentiation. In sundamaged skin, the numerous foci of abnormal growths and segments of atypical, abnormal epidermis are corrected, reversed or eliminated. Fewer growths appear and progression to cancer is halted. Normalizing of the epidermis results in a smoother, less dry and rough skin, since cells are not only produced more rapidly, but exfoliation occurs by individual cells rather than in clusters or scales, thus improving the topography of the skin. Moreover, hyperpigmentary blotches and splotches are reduced by retinoids, eliminating the mottled appearance of sundamaged skin.

(c) The metabolism of fibroblasts is increased. Fibroblasts synthesize the fibers of the dermis; new collagen is laid down, strengthening the physical foundation of the skin. Fibroblasts also make the ground substance which exists between the fibers, allowing these to glide past each other. The ground substance, known as acid mucopolysaccharides, is also responsible for the turgor and bounce of the skin. Retinoids stimulate the formation of new acid mucopolysaccharides.

Accordingly, retinoids promote the formation of a more normal dermis. Because of this activity, they have been found to promote and accelerate the healing of wounds in compromised tissue, of which aged dermis is an example. Further, the production of a new collagen layer not only repairs damaged skin but results in the effacement and prevention of fine wrinkles and lines.

(d) Vascularity is increased. Retinoids stimulate blood flow and promote the formation of new vessels. Blood flow is greatly reduced in aged, sundamaged skin. A brisker blood supply improves the physiologic competence of the skin and imparts a livelier, glowing appearance. Patients often say their skin feels "more alive".

Several of the prior art treatments using retinoic acid as referred to above have claimed there is an increase in the blood flow in the skin. However, the increased blood flow from such short term treatments could result simply from vasodilation caused by the irritating effects of high concentrations of the acid. In contrast, the low sub-irritating concentrations of retinoids according to the present invention do not cause significant vasodilation. Over the long term there occurs formation of many new small blood vessels, markedly increasing the functional blood supply to the skin. As a result, the skin can react more effectively to external sources of damage and can then mount a more normal inflammatory response to fight infection. The increased blood supply allows the skin to clear irritants and toxins more quickly.

Still further, treatment with retinoids according to the present invention raises the surface temperature of the skin by about 1/2 degree centigrade due to greater flow of blood. The increased blood flow also increases acuity to pain and irritation, and the skin becomes more reactive to chemical insults. For example, experiments with highly drying and irritating cosmetics, soaps, perfumes, etc. have shown that young people will experience severe irritation within 3 or 4 days whereas it may take 2 to 3 weeks for an older person to note the same irritation. The increased sensitivity of the skin treated with retinoids provides an early warning system to older people so that too much damage is not done before the pain or irritation is felt.

Retinoids have been defined narrowly as comprising simply vitamin A (retinol) and its derivatives such as vitamin A aldehyde (retinal), vitamin A acid (retinoic acid), comprising the so called natural retinoids. However, subsequent research has resulted in a much larger class of chemical compounds that are termed retinoids due to their biological similarity to vitamin A and its derivatives. Compounds useful in the present invention include all natural and/or synthetic analogues of vitamin A or retinol-like compounds which possess the biological activity of vitamin A in the skin, such as the control of epithelial cell differentiation of keratinocytes in the epidermis and/or stimulation of fibroplasia or new collagen synthesis in the dermis among other effects. Accordingly, as used herein for purposes of the present invention, the term "retinoid" will be understood to include any of the foregoing compounds. Examples of suitable retinoids for use in the present invention are set forth in Table I, although it will be understood that the invention is not limited thereto.

TABLE I

| Chemical, Common and/or Commmercial Name |
| --- |
| Isotretinoin |
| 13-cis-retinoic acid |
| ACCUTANE |
| Etretinate |
| TEGISON |
| (all-E)-9-(4-methoxy-2,3,6-trimethylphenyl)-3,7-dimethyl-2,4,6,8-nonatetraenoic acid ethyl ester |
| Etretin |
| (all-E)-9-(4-methoxy-2,3,6,-trimethylphenyl)-3,7-dimethyl-2,4,6,8,-nonatetraenoic acid |
| Motretinide |
| N—ethyl-9-(4-methoxy-2,3,6-trimethylphenyl)-3,7-dimethyl-2,4,6,8-nonatetraenamide |
| (E,E)-9-(2,6-dichloro-4-methoxy-3-methylphenyl)-3,7-dimethyl-2,4,6,8-nonatetraenoic acid ethyl ester |
| 7,8-didehydroretinoic acid |
| (E,E)-4-[2-methyl-4-(2,6,6-trimethyl-1-cyclohexen-1-yl)-1,3-butadienyl] benzoic acid |
| (E)-4-[4-methyl-6-(2,6,6-trimethyl-1-cyclohexen-1-yl-)-1,3,5-hexatrienyl] benzoic acid |
| (all-E)-3,7-dimethyl-9-(3-thienyl)-2,4,6,8-nonatetraenoic acid |
| (E,E,E)-3-meyl-7-(5,6,7,8-tetrahydro-5,5,8-tetramethyl-2-naphthlenyl)-2,4,6-octatrienoic acid |
| (E)-6-[2-(2,6,6-trimethyl-1-cyclohexen-1-yl)ethenyl)]-2-naphthalenecarboxylic acid |
| (E,E,E)-7-(2,3-dihydro-1,1,3,3-tetramethyl-1H—inden-5-yl)-3-methyl-2,4,6-octatrienoic acid |
| (E)-4-(2,3-dihydro-1,1,3,3-tetramethyl-1H—inden-5-yl)-1-propenyl] benzoic acid |
| TTNPB |
| (E)-4-[2-(5,6,7,8-tetrahydro-5,5,8,8-tetramethyl-2-naphthalenyl-1-propenyl] benzoic acid |
| (E)-4-[2-(5,6,7,8-tetrahydro-3-methyl-5,5,8,8-tetramethyl-2-naphthalenyl-1-propenyl] benzoic acid |
| (E)-1,2,3,4-tetrahydro-1,1,4,4-tetramethyl-6-(1-methyl-2-phenylethel) naphthalene |
| 6-(1,2,3,4-tetrahydro-1,1,4,4-tetramethyl-6-naphthyl)-2-naphthalene- |

TABLE I-continued

| Chemical, Common and/or Commmercial Name |
| --- |
| carboxylic acid |
| (E)-6-[2-[4-(ethylsulfonly)phenyl-<br>1-methylethenyl]-1,2,3,4-tetrahydro-<br>1,1,4,4-tetramethylnaphthalene |
| 4-[(5,6,7,8-tetrahydro-5,5,8,8-<br>tetramethyl-2-naphthalenyl)ethynyl]<br>benzoic acid |
| (E)-2-(1,1,4,4-tetramethyl-1,2,3,4-<br>tetrahydronaphth-7-y-1-[4-<br>tetrazol-5-yl)phenyl]-1-propene |
| (E)-4-[2-(5,6,7,8-tetrahydro-7-<br>hydroxy-5,5,8,8-tetramethyl-2-<br>naphthalenyl)-1-propenyl]<br>benzyl alcohol |
| AM-80 |
| 2-(4-Carboxybenzamido)-5,6,7,8-<br>t@etrahydro-5,5,8,8-tetramethylnaphthalene |
| AM-580 |
| 2-[N—(4-Carboxyphenyl)carbamoyl]-<br>5,6,7,8-tetrahydro-5,5,8,8-tetramethyl-<br>naphthalene |
| CH-55 |
| 1-[3,5-(Di-tert-butyl)benzoyl]-2-(4-<br>Carboxyphenyl)ethene |
| TTNT |
| 2-(5,6,7,8-tetrahydro-5,5,8,8-<br>tetramethyl-2-naphthyl)-6-benzo(b) thiophene<br>carboxylic acid |
| TTNF |
| 2-(5,6,7,8-tetrahydro-5,5,8,8-<br>tetramethyl-2-naphthyl)-6-benzo(b)<br>furancarboxylic acid |
| TTNI |
| 2-(5,6,7,8-tetrahydro-5,5,8,8-<br>tetramethyl-2-naphthyl)-6-indole-<br>carboxylic acid |
| TTNN |
| 2-(5,6,7,8-tetrahydro-5,5,8,8-<br>tetramethyl-2-naphthyl)-6-naphthalene<br>carboxylic acid |
| p-(5,6,7,8-tetrahydro-5,5,8,8-<br>tetramethyl-2-anthracenyl) benzoic acid |
| Esters or amides of 13-trans retinoic<br>acid or 13-cis retinoic acid wherein the<br>—OH group of the carboxylic acid (—COOH)<br>group is substituted by —OR$^1$ or NR$^2$R$^3$,<br>wherein R$^1$, R$^2$ and R$^3$ are such that<br>these esters or amides can be converted<br>to 13-trans retinoic acid or 13-cis<br>retinoic acid through hydrolysis,<br>metabolism, cleavage, etc. |

Also encompassed within the term "retinoid" are geometric and stereoisomers of the retinoids. For example, in my U.S. Pat. No. 4,603,146 in which vitamin A acid was used as the active ingredient, the specific examples used tretinoin (all-trans retinoic acid). However, according to the present invention it has been found that isotretinoin (13-cis-retinoic acid) may also be used, although somewhat higher concentrations are needed to obtain equivalent results.

Retinoids may be formulated in bland, moisturizing bases, such as creams or ointments, usually in low concentrations, although higher concentrations may be used for darker skins. For example, isotretinoin may be used in concentrations of about 0.01% to 0.3% and preferably about 0.04% to 0.1% by weight of the base.

Other non-toxic, dermatologically acceptable vehicles or carriers in which retinoids are stable will be evident to those of ordinary skill in the art. In general, emollient or lubricating vehicles, such as oleaginous substances, which help hydrate the skin are preferred. As used herein, the term "emollient" will be understood to refer to the non-irritating character of the composition as a whole. That is, the nature of the vehicle and amount of retinoid therein should be selected so as to provide a sub-irritating dose for topical application. Volatile vehicles which dry or otherwise harm the skin, such as alcohol and acetone, should be avoided.

An ointment base (without water) is preferred in the winter and in subjects with very dry skin. Examples of suitable ointment bases are petrolatum, petrolatum plus volatile silicones, lanolin, and water in oil emulsions, such as Eucerin (Beiersdorf).

In warm weather and often for younger persons, oil in water emulsion (cream) bases, are preferred. Examples of suitable cream bases are Nivea Cream (Beiersdorf), cold cream (USP), Purpose Cream (Johnson & Johnson), hydrophilic ointment (USP), and Lubriderm (Warner-Lambert).

Some retinoids are mild irritants and may cause redness and scaling, which may be accompanied by some tenderness and tightness. These reactions are transient and quickly disappear when the applications are stopped. However, the skin rapidly accomodates, and even when retinoids are applied excessively to produce visible inflammation, the reaction slowly disappears leaving no permanent sequellae. Systemic side reactions are unknown and are not to be expected from such low concentrations according to the present invention. Selection of an appropriate emollient vehicle will more readily allow the use of a highly effective but sub-irritating dose of the retinoid.

The length of treatment according to the present invention may best be described as indefinite. That is, compared to the short term prior art treatments of various conditions with retinoids in which the treatments were terminated as soon as the condition cleared, the present invention requires treatment to be continued indefinitely since the aging process continues indefinitely. Also, the benefits of treatment slowly fade after the treatment is stopped. The treatment of the present invention may be considered to be intervention therapy in decelerating the aging process. If the intervention is stopped, there is regression to the original state. Hence, a maintenace regimen is required.

Usually, there is little point in beginning the treatments of the present invention until young adult life or, more typically, in middle age, when the effects of aging begin to appear. The particular program of maintenance therapy according to the present invention will vary depending upon the individual and conditions being treated. Generally, depending upon the age and state of the skin when treatments begin, it has been found that once a day applications of retinoids for up to 6 to 8 months may be necessary to reduce and control the effects of aging which have already occurred. Once a stabilized skin control has been obtained, the frequency of application of the retinoids may be reduced, for example to two or three times a week, and in some cases only once a week for the rest of the person's life. That is, once the aging process has been controlled, a maintenance dose on the order of two applications per week is generally sufficient to maintain that state.

The invention will now be illustrated in more detail by reference to the following specific, non-limiting examples:

EXPERIMENTAL EXAMPLE 1

Twenty-six middle-aged women, 35 to 55 years old, with actinically damaged skin, received once daily applications to the entire face of 0.05% 13-cis-retinoic acid in Purpose Cream for a period of 4 to 6 months. All had wrinkles, blotches and elastosis. The treatment caused neither redness nor drying of the skin. The treatment also was better tolerated than similar treatments with 0.05% all-trans retinoic acid in a cream base as disclosed in my co-pending application. The application of 13-cis-retinoic acid resulted in smoother skin in which fine wrinkles were moderately effaced.

EXPERIMENTAL EXAMPLE 2

Applications were made in the same way as Example 1 with 0.25% 13-cis-retinoic acid in Purpose Cream to the faces of eight women with photodamaged skin. The treatment was better tolerated (less irritancy was noted) than similar treatments of 0.05% tretinoin in a cream base as disclosed in my co-pending application. The treatments resulted in the obvious elimination of fine wrinkles. In addition, the skin appeared to have greater turgor to the palpating finger. The subjects of the study expressed satisfaction with the results of the treatment. The experimental results indicate that the application of 0.25% 13-cis-retinoic acid in Purpose Cream to be about as effective as 0.05% tretinoin in a cream base. Thus, 13-cis-retioic acid has the capacity to achieve the same beneficial effects as retinoic acid on photoaged skin. Since the 13-cis-retinoic acid is apparently less effective at equal concentrations, biological equivalence can be obtained by increasing the concentration of 13-cis-retinoic acid 4 to 5 fold.

1 EXPERIMENTAL EXAMPLE 3

A histologic study was conducted on male and female subjects 45 to 60 years of age, with a history of excessive sun exposure and clinical evidence of photodamaged skin, to compare the two retinoids 0.05% 13-cis-retinoic acid in Purpose Cream and 0.05% tretinoin in cream base. Each of the seven subjects received a once daily application for three months of 0.05% 13-cis-retinoic acid in Purpose Cream to one dorsal forearm and 0.05% tretinoin cream to the other dorsal forearm. Following the three month treatment period a 4 millimeter punch biopsy was obtained from the forearms of each subject. The specimens obtained were fixed in formalin and prepared for light microscopy both by paraffin and methacrylate embedding.

The specimens of the forearms were compared in regard to the following histological features.
(1) Thickening of the epidermis.
(2) Correction of epidermal atypia and cytologic abnormalities.
(3) New blood vessels.
(4) Dispersion of melanin pigment.
(5) Decrease in number of horny cells.
(6) Expansion of the sub-epidermal Grenz zone, reflecting new collagen formation.

The results of the histological study are summarized as follows. In five of the seven subjects, histologic changes characteristic of 0.05% retinoic acid were evident on the forearm treated with tretinoin cream. Similar changes were observed in only three of the 0.05% 13-cis-retinoic acid-treated forearms and in each case were of substantially lesser magnitude. The epidermal alterations of the 13-cis-retinoic acid treatment were more noticeable than retinoic acid especially in improvement of cytologic irregularities. The dermis, by contrast, was scarcely altered with the 13-cis-retinoic acid treatment. The results of the study indicate that 0.05% 13-cis-retinoic acid is inferior to 0.05% retinoic acid in correcting photodamage.

EXPERIMENTAL EXAMPLE 4

A histologic study was conducted on male and female subjects 45 to 60 years of age with a history of excessive sun exposure and clinical evidence of photodamaged skin to compare two retinoids, 0.25% 13-cis-retinoic acid in Purpose Cream and 0.05% tretinoin in cream base. Each of the six subjects received a once daily application for three months of the two retinoids, 13-cis-retinoic acid and all-trans retinoic acid, to opposite forearms. The procedures used in this study and the parameters analyzed are identical to those described in Example 3.

The results of the histologic study indicate that all six individuals responded adequately to the 0.05% all-trans retinoic acid with marked thickening of both the epidermis and the Grenz zone. Equivalent histologic changes were observed in the 0.25% 13-cis-retinoic acid treated specimens. Thus the two treatments were histologically indistinguishable. Therefore, the difference between the two retinoids is merely quanitative in that 13-cis-retinoic acid is less potent than all-trans retinoic acid. The difference between the two retinoids can be overcome by increasing the concentration of 13-cis-retinoic acid to make both compounds biologically equivalent.

From the foregoing embodiments, and the disclosure of my co-pending application incorporated herein by reference it will be seen that the invention has the following advantages inter alia:
A. Clinical
Effacement of fine wrinkles
Smoother surface
Lightens pigmented blotches
Skin has more turgor
Large pores less noticeable
Skin feels livelier
B. Histologic
Thicker epidermis
Normalizes atypia and pre-malignant changes
Atrophy and dysplasia corrected
Stimulates blood flow; new vessels formed
Stimulates fibroblasts with new collagen formation
Increases ground substance
Melanin within keratinocytes is decreased It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim:
1. A method for retarding and reversing the loss of collagen fibers, abnormal changes in elastic fibers, and deterioration of small blood vessels in sundamaged human skin, comprising applying topically to the surface of the skin a composition comprising effective amounts of a retinoid selected from the group consisting of 2-(4-Carboxybenzamido)-5,6,7,8-tetrahydro-5,5,8,8-tetramethylphaphthalene; 2-[N-(4-Carboxyphenyl)carbamoly]-5,6,7,8-tetrahydro-5,5,8,8-tetramethyll-naphthalene; 1-[3,5-(Di-tert-butyl)benzoyl]-2-(4-Carboxyphenyl)ethene; TTNT 2-(5,6,7,8-tetrahydro-5,5,8,8-tet- ramethyl-2-naphthyl)-6-benzo (b) thiophene carboxylic acid; TTNF 2-(t,6,7,8-tetrahydro-5,5,8,8-tetramethyl-2-naphthyl)-6-benzo (b) furancarboxylic acid; TTNI 2-(5,6,7,8-tetraphydro-5,5,8,8-tetramethyl-2-naphthyl)-6-indolecarboxylic acid; TTNN 2-(5,6,7,8-tetrahydro-5,5,8,8-tetramethyl-2naphthyl)-6-naphthalene carboxylic acid; p-(5,6,7,8-tetrahydro-5,5,8,8-tetramethyl-2-anthracenyl) benzonic acid; and esters or amides of 13 trans retinoic acid or 13-cis retinoic acid wherein the —OH group of the carboxylic acid (—COOH) group is substituted by —OR$^1$ or NR$^2$R$^3$, wherein R$^1$, R$^2$ and R$^3$ are such that these esters or amides can be converted to 13-trans retinoic acid or 13-cis retinoic acid through hydrolysis, metabolism, or cleavage, in a non-toxic, dermatologically acceptable vehicle in a program of maintenance therapy, whereby the skin substantially regains and maintains its firmness, turgor and elasticity during said therapy, said composition and amounts of retinoid therein being selected so as to provide a dose for application which is insufficient to cause excessive irritation.

2. A method according to claim 1 wherein said skin is human facial skin.

3. A method according to claim 1 wherein said vehicle is an emollient vehicle.

4. A method according to claim 1 wherein said dose is a sub-irritating dose.

* * * * *